US00PP23790P2

(12) United States Plant Patent
Dümmen

(10) Patent No.: US PP23,790 P2
(45) Date of Patent: Jul. 30, 2013

(54) ***PELARGONIUM* PLANT NAMED 'DUEPAWITEIMP'**

(50) Latin Name: *Pelargonium peltatum*
Varietal Denomination: Duepawiteimp

(75) Inventor: Tobias Dümmen, Rheinberg (DE)

(73) Assignee: Capital Green Investments Ltd., Grand Cayman (KY)

( * ) Notice: Subject to any disclaimer, the term of this patent is extended or adjusted under 35 U.S.C. 154(b) by 77 days.

(21) Appl. No.: 13/317,918

(22) Filed: Oct. 31, 2011

(51) Int. Cl.
*A01H 5/00* (2006.01)

(52) U.S. Cl.
USPC ..... Plt./332

(58) Field of Classification Search
USPC ..... Plt./332
See application file for complete search history.

*Primary Examiner* — Annette Para
(74) *Attorney, Agent, or Firm* — C. A. Whealy

(57) ABSTRACT

A new and distinct cultivar of Ivy Geranium plant named 'Duepawiteimp', characterized by its upright to outwardly spreading plant habit; vigorous growth habit; freely basal branching habit; freely flowering habit; large light pink-colored semi-double flowers; and good garden performance.

1 Drawing Sheet

Botanical designation: *Pelargonium peltatum.*
Cultivar denomination: 'DUEPAWITEIMP'.

BACKGROUND OF THE INVENTION

The present invention relates to a new and distinct cultivar of Ivy Geranium plant, botanically known as *Pelargonium peltatum*, and hereinafter referred to by the name 'Duepawiteimp'.

The new Ivy Geranium plant is a product of a planned breeding program conducted by the Inventor in Rheinberg, Germany. The objective of the breeding program is to create new freely-branching Ivy Geranium plants with dark green-colored leaves and attractive flowers.

The new Ivy Geranium plant originated from a cross-pollination made by the Inventor in July, 2007 in Rheinberg, Germany of a proprietary selection of *Pelargonium peltatum* identified as code number F-02-018, not patented, as the female, or seed, parent with a proprietary selection of *Pelargonium peltatum* identified as code number F-19-0114, not patented, as the male, or pollen, parent. The new Ivy Geranium plant was discovered and selected by the Inventor as a single flowering plant from within the progeny of the stated cross-pollination in a controlled greenhouse environment in Rheinberg, Germany in May, 2010.

Asexual reproduction of the new Ivy Geranium plant by vegetative terminal cuttings in a controlled greenhouse environment in Rheinberg, Germany since June, 2010 has shown that the unique features of this new Ivy Geranium plant are stable and reproduced true to type in successive generations.

SUMMARY OF THE INVENTION

Plants of the new Ivy Geranium have not been observed under all possible environmental conditions and cultural practices. The phenotype may vary somewhat with variations in environmental conditions such as temperature and light intensity without, however, any variance in genotype.

The following traits have been repeatedly observed and are determined to be the unique characteristics of 'Duepawiteimp'. These characteristics in combination distinguish 'Duepawiteimp' as a new and distinct Ivy Geranium plant:

1. Upright to outwardly spreading plant habit.
2. Vigorous growth habit.
3. Freely basal branching habit.
4. Freely flowering habit.
5. Large light pink-colored semi-double flowers.
6. Good garden performance.

Plants of the new Ivy Geranium differ primarily from plants of the female parent selection in the following characteristics:

1. Plants of the new Ivy Geranium are more compact than plants of the female parent selection.
2. Plants of the new Ivy Geranium are more freely branching than plants of the female parent selection.
3. Plants of the new Ivy Geranium and the female parent selection differ slightly in flower color.

Plants of the new Ivy Geranium differ primarily from plants of the male parent selection in the following characteristics:

1. Plants of the new Ivy Geranium are more freely branching than plants of the male parent selection.
2. Plants of the new Ivy Geranium and the male parent selection differ slightly in flower color.

Plants of the new Ivy Geranium can be compared to plants of *Pelargonium peltatum* 'Guitoublanc', disclosed in U.S. Plant Pat. No. 9,728. In side-by-side comparisons conducted in Rheinberg, Germany, plants of the new Ivy Geranium differed primarily from plants of 'Guitoublanc' in the following characteristics:

1. Plants of the new Ivy Geranium were more compact than plants of 'Guitoublanc'.
2. Plants of the new Ivy Geranium were more freely branching than plants of 'Guitoublanc'.
3. Plants of the new Ivy Geranium had slightly larger leaves than plants of 'Guitoublanc'.
4. Plants of the new Ivy Geranium were more freely flowering than plants of 'Guitoublanc'.

5. Plants of the new Ivy Geranium and 'Guitoublanc' differed slightly in flower color.

BRIEF DESCRIPTION OF THE PHOTOGRAPH

The accompanying colored photograph illustrates the overall appearance of the new Ivy Geranium plant showing the colors as true as it is reasonably possible to obtain in colored reproductions of this type. Colors in the photograph may differ slightly from the color values cited in the detailed botanical description which accurately describe the colors of the new Ivy Geranium plant. The photograph comprises a side perspective view of a typical flowering plant of 'Duepawite-imp' grown in a container.

DETAILED BOTANICAL DESCRIPTION

The aforementioned photograph and following observations and measurements describe plants grown during the summer in 12-cm containers in a glass-covered greenhouse in Rheinberg, Germany and under cultural practices which closely approximate commercial *Pelargonium* production. During the production of the plants, day and night temperatures averaged 18° C. and light levels averaged 4,500 lux. Plants were pinched one time three weeks after planting and were 13 weeks old when the photograph and the description were taken. In the detailed description, color references are made to The Royal Horticultural Society Colour Chart, 1995 Edition, except where general terms of ordinary dictionary significance are used.

Botanical classification: *Pelargonium peltatum* 'Duepawite-imp'.

Parentage:

*Female, or seed, parent*.—Proprietary selection of *Pelargonium peltatum* identified as code number F-02-018, not patented.

*Male or pollen parent*.—Proprietary selection of *Pelargonium peltatum* identified as code number F-19-0114, not patented.

Propagation:

*Type*.—By vegetative terminal cuttings.

*Time to initiate roots, summer*.—About five days at temperatures of about 20° C.

*Time to initiate roots, winter*.—About seven days at temperatures of about 20° C.

*Time to produce a rooted young plant, summer*.—About three weeks at temperatures of about 20° C.

*Time to produce a rooted young plant, winter*.—About four weeks at temperatures of about 20° C.

*Root description*.—Fine, fibrous; white in color.

*Rooting habit*.—Freely branching; dense.

Plant description:

*General appearance*.—Upright to outwardly spreading plant habit; uniformly rounded; densely foliated.

*Growth and branching habit*.—Vigorous growth habit; freely basal branching habit with about three basal branches developing per plant.

*Plant height to top of flower umbels*.—About 30 cm.

*Plant height to top of foliar plane*.—About 26.5 cm.

*Plant width*.—About 23 cm.

*Lateral branches*.—Length: About 13 cm. Diameter: About 7 mm. Internode length: About 2.8 cm. Texture: Pubescent. Strength: Moderately strong. Color: Close to 144A.

Foliage description:

*Arrangement*.—Alternate; simple.

*Length*.—About 6.3 cm.

*Width*.—About 7.4 cm.

*Shape*.—Reniform.

*Apex*.—Acute.

*Base*.—Peltate.

*Margin*.—Crenate.

*Venation pattern*.—Palmate.

*Texture, upper surface*.—Pubescent.

*Texture, lower surface*.—Smooth, glabrous.

*Color*.—Developing leaves, upper surface: Close to 137B. Developing leaves, lower surface: Close to 147B. Fully expanded leaves, upper surface: Close to 147A; venation, close to 143B. Fully expanded leaves, lower surface: Close to 147B; venation, close to 143B. Zonation pattern: Location: Towards the leaf base. Color: Close to 187A.

*Petiole*.—Length: About 4.9 cm. Diameter: About 3 mm. Texture, upper and lower surfaces: Smooth, glabrous. Color, upper surface: Close to 143A. Color, lower surface: Close to 143B.

Flower description:

*Flower arrangement*.—Semi-double rotate flowers arranged in rounded hemispherical umbels arising from apical leaf axils; umbels displayed above the foliage on moderately strong peduncles; flowers face upright to outward.

*Fragrance*.—None detected.

*Quantity of flowers*.—Freely flowering habit; about nine flowers per umbel.

*Flowering season*.—Year-round under greenhouse conditions; in outdoor nurseries and gardens in Germany, flowering is continuous from spring throughout the summer; plants begin to flower about eight weeks after planting.

*Flower longevity*.—Individual flowers last about five to seven days on the plant; flowers persistent.

*Umbel height*.—About 5 cm.

*Umbel diameter*.—About 8 cm.

*Flower diameter*.—About 4.5 cm.

*Flower depth (height)*.—About 2.5 cm.

*Flower buds*.—Length: About 1.6 cm. Diameter: About 7 mm. Shape: Ovoid. Color: Close to 36D.

*Petals*.—Quantity per flower: About five. Length: About 2.5 cm. Width: About 1.7 cm. Shape: Obovate. Apex: Rounded. Base: Attenuate. Margin: Sinuate. Texture, upper and lower surfaces: Smooth, glabrous. Color: When opening, upper surface: Close to 56B. When opening, lower surface: Close to 36D. Fully opened, upper surface: Close to 56D; towards the base and venation, close to 61 A. Fully opened, lower surface: Close to 36D.

*Petaloids*.—Quantity per flower: About three. Length: About 2.1 cm. Width: About 9 mm. Shape: Obovate. Apex: Rounded. Base: Attenuate. Margin: Sinuate. Texture, upper and lower surfaces: Smooth, glabrous. Color: When opening, upper surface: Close to 56B. When opening, lower surface: Close to 36D. Fully opened, upper surface: Close to 56D; towards the base and venation, close to 61A. Fully opened, lower surface: Close to 36D.

*Sepals*.—Quantity per flower: Five, arranged in a single whorl. Length: About 1.3 cm. Width: About 4 mm. Shape: Ensiform. Apex: Apiculate. Base: Attenuate. Margin: Entire. Color, upper and lower surfaces: Close to 144A.

*Peduncle* (*umbel stem*).—Length: About 9 cm. Diameter: About 3 mm. Strength: Moderately strong. Texture: Smooth, glabrous. Color: Close to 144A.

*Pedicel* (*individual flower stem*).—Length: About 2.2 cm. Diameter: About 2 mm. Strength: Moderately strong. Texture: Pubescent. Color: Close to 144A.

*Reproductive organs*.—Androecium: Stamen quantity per flower: About seven. Filament length: About 7 mm. Filament color: Close to 49D. Anther length: About 3 mm. Anther shape: Oval. Anther color: Close to 166A. Pollen amount: Moderate. Pollen color: Close to 28A. Gynoecium: Pistil quantity per flower: One. Pistil length: About 9 mm. Stigma shape: Parted. Stigma color: Close to 54A. Style length: About 2 mm. Style color: Close to 49D. Ovary color: Close to 148C.

*Seeds and fruits*.—Seed and fruit development have not been observed on plants of the new *Pelargonium*.

Disease/pest resistance: Plants of the new Ivy Geranium have not been observed to be resistant to pathogens and pests common to Ivy Geraniums.

Garden performance: Plants of the new Ivy Geranium have been observed to tolerate rain, wind, and temperatures ranging from about 5° C. to about 40° C. and have demonstrated good garden performance.

It is claimed:

1. A new and distinct Ivy Geranium plant named 'Duepawiteimp' as illustrated and described.

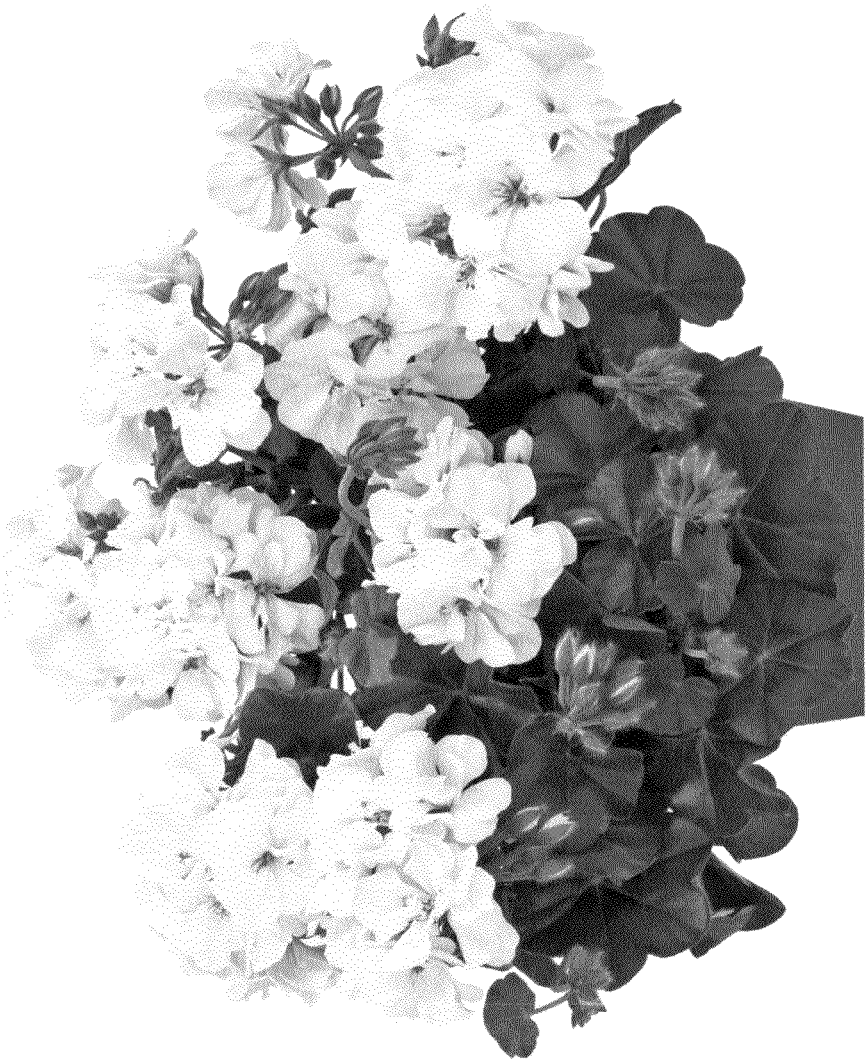

* * * * *